United States Patent [19]

Nemeth et al.

[11] Patent Number: 5,466,835
[45] Date of Patent: * Nov. 14, 1995

[54] TITANOSILICATE AS AN EPOXIDATION CATALYST FOR OLEFINS

[75] Inventors: Laszlo T. Nemeth, Palatine; Thomas P. Malloy, Lake Zurich; Richard R. Jones, Bensenville, all of Ill.

[73] Assignee: UOP, Des Plaines, Ill.

[ * ] Notice: The portion of the term of this patent subsequent to Oct. 11, 2011, has been disclaimed.

[21] Appl. No.: 239,801

[22] Filed: May 9, 1994

Related U.S. Application Data

[63] Continuation-in-part of Ser. No. 172,314, Dec. 23, 1993, Pat. No. 5,354,875.

[51] Int. Cl.$^6$ .................. C07D 301/12; C07D 301/14; C07D 301/19; C07D 303/04
[52] U.S. Cl. .................. 549/531; 502/242; 549/525; 549/529
[58] Field of Search .................. 549/531, 529, 549/525

[56] References Cited

U.S. PATENT DOCUMENTS

| | | | |
|---|---|---|---|
| 4,410,501 | 10/1983 | Taramasso et al. | 423/326 |
| 4,410,715 | 10/1983 | McMullen et al. | 549/531 |
| 4,833,260 | 5/1989 | Neri et al. | 549/531 |
| 5,214,168 | 5/1993 | Zajacek et al. | 549/531 |

FOREIGN PATENT DOCUMENTS 526945 3/1992 European Pat. Off. .

OTHER PUBLICATIONS

Notari, B., *Innovation in Zeolite Materials Science*, Grobet, P. J. et al., Ed.,; Elsevier: Amsterdam, pp. 413–425 (1988).
A. J. H. P. van der Pol et al., *Appl. Catal.*, A92 (1992), 113–130.

*Primary Examiner*—Joseph E. Evans
*Attorney, Agent, or Firm*—Thomas K. McBride; Eugene I. Snyder

[57] ABSTRACT

The oxidation of olefinic compounds generally using hydroperoxides, especially aqueous solutions of hydrogen peroxide, can be effected in high yield and with good selectivity in the presence of a catalyst which is a mixture of small particles of titania and a titanosilicalite. Small particle size is essential in affording a catalyst with good activity and selectivity, with particle sizes no more than about 0.3 microns being the preferred mode of operation. Dilute aqueous hydrogen peroxide solutions may be used with good results. The resulting epoxidation, even when carried out at modest temperatures and with dilute aqueous hydrogen peroxide solutions, afford superior results in epoxidation relative to TS-1.

17 Claims, No Drawings

TITANOSILICATE AS AN EPOXIDATION CATALYST FOR OLEFINS

CROSS REFERENCE TO RELATED APPLICATIONS

This application is a continuation-in-part of my application U.S. Ser. No. 08/172,314 filed Dec. 23, 1993, now U.S. Pat. No. 5,354,875, all of which is incorporated by reference.

BACKGROUND OF THE INVENTION

One of the most challenging and formidable tasks in preparative organic chemistry is the selective functionalization of hydrocarbons. Once a functional group has been introduced, the chemist has a rich selection of tools to achieve further transformations and transpositions, but the initial barrier of introducing a functional group is determinative of further chemistry. Not only is it necessary that a given functionalization reaction proceeds in good yield, but it is necessary also that it proceeds with specificity. One of the most chemically attractive entry points to functionalization of hydrocarbons is the carbon-carbon double bond in alkanes and substituted alkenes, for the carbon-carbon double bond undergoes many reactions which introduce functional groups onto one or both of the carbons, and the double bond also activates an adjacent C-H bond (i.e., allylic hydrogen) to still other reactions. Among the chemical reactions of the carbon-carbon double bond that of epoxidation occupies a special niche, because epoxidation is virtually unique to the C=C linkage, because epoxidation proceeds with great specificity, and because the resulting epoxide is a controllably reactive functional group which reacts with a wide range of reagents, schematically represented here as H-Y, to afford an equally wide range of difunctional materials according to the reaction,

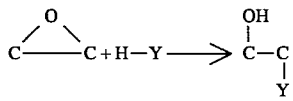

Although epoxidation may be performed with several different reagents, that variation of greatest interest here is one where the reagent is a hydroperoxide, particularly where epoxidation is catalyzed by a titanium compound. A commercial process uses tertiary butyl or ethylbenzene hydroperoxide in combination with 2% titania supported on silica to epoxidize propylene to propylene oxide with greater than 97% conversion of, for example, ethylbenzene hydroperoxide and selectivities to propylene oxide formation approaching 90%. See U.S. Pat. No. 3,642,833, 3,923,843, 4,021,454 and 4,367,342, all assigned to Shell Oil Company. More recently an Italian group has developed catalysts, referred to as titanium silicalites, where small amounts of framework silicon in silicalite are said to be replaced by titanium [Taramasso et al., U.S. Pat. No. 4,410,501] and has found such materials, conveniently designated as TS-1, to be effective in catalyzing the epoxidation of olefinic compounds by hydrogen peroxide in either the presence or absence of a solvent; U.S. Pat. No. 4,833,260. Subsequently this has been extended to the epoxidation of olefins with oxygen in air in the presence of a redox system of alkyl anthrahydroquinone and alkyl anthraquinone; EP 526,945.

Notaft, B., Innovation in Zeolite Materials Science; Grobet, P. J. et al., Ed.,; Elsevier: Amsterdam, pp. 422–424 has speculated that the observed catalytic activity both of titania supported on silica and TS-1 arises from the high dispersion of titanium atoms in a silica lattice, that is, active materials are characterized by Ti(IV) isolated by a long sequence of -O-Si-O-Si-. This conclusion was supported somewhat by the observation that when titania is supported on alumina, magnesia, or zirconia the resulting composite is inactive in epoxidation, and also is supported by the observation that catalyst activity increases as manifested by an increase in epoxide selectivity as the concentration of titania on silica decreases. Catalytic activity of TS-1 in the hydroxylation of phenol also has been shown to be dependent on particle size (A. J. H. P. van der Pol et al., Appt Catal., A92 (1992), 113–130) with particles in the 0.2–0.3 micron range being 10 times more active than those in the 5 micron range.

What we have observed is that particular mixtures of a titanosilicate and titania are demonstrably more active and more selective as a catalyst in the epoxidation of olefinic compounds than are prior art titanium-based catalysts which have been used in epoxidation. Whether the titanosilicate is analogous to the "titanium silicalite" exemplified by TS-1 may be open to dispute. What is not a matter of dispute is its greatly increased activity, selectivity, and reusability relative to TS-1. We believe that these characteristics make the catalysts of our invention uniquely suited for use in the epoxidation of olefins with hydrogen peroxide.

SUMMARY OF THE INVENTION

One purpose of this invention is to devise a facile, efficient process for the conversion of olefins generally to their epoxides in high yield and with great selectivity. One embodiment is the epoxidation of an olefinic compound by hydrogen peroxide using as a catalyst a mixture of titania and titanosilicalite particles, each of which has an average diameter no greater than about 0.3 microns. In a more specific embodiment the epoxidation is conducted in purely aqueous media using hydrogen peroxide at a concentration no more than about 30 weight percent. In a more specific embodiment the epoxidation is effected with hydrogen peroxide at a concentration no more than about 15 weight percent and at a temperature no more than about 100° C. In yet another embodiment the olefinic compound is propylene. Other embodiments will become apparent from the ensuing description.

DESCRIPTION OF THE INVENTION

We have found that certain mixtures of titanosilicates and titania are extraordinarily effective catalysts in the epoxidation of olefinic compounds using hydroperoxides as the epoxidizing agent. Hydrogen peroxide can be readily utilized, even at concentrations as low as about 2 weight percent, and epoxidations often take place at a convenient rate at temperatures in the range of 25°–75° C.

The feedstock for this reaction contains olefinic compounds generally, with or without a solvent. The olefinic compound can be generally described according to the formula

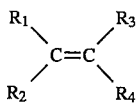

where $R_1$, $R_2$, $R_3$, and $R_4$ may be hydrogen, alkyl, aryl, cycloalkyl, aralkyl, carboxylic acid, carboalkoxy, a halogen, sulfonic acid, sulfonic acid ester, nitrile, sulfone, or ether group. The alkyl, cycloalkyl, arylalkyl, or aryl groups also may contain, e.g., a carboxylic acid grouping, carboxylic ester grouping, halogen, sulfonic acid or sulfonic ester grouping, nitrile, nitro, hydroxyl, ketone, anhydride, amino, hydroxyl, and ether groupings. As can be appreciated, our invention is applicable to an enormous diversity of olefinic compounds. In fact, the major criterion for a suitable feedstock is that is contain a non-aromatic carbon-carbon double bond.

One large group of olefinic compounds which may be used in the practice of our invention are the alkenes, especially those containing between about 2 and 20 carbon atoms. Such alkenes include ethylene, propylene, butene-1, butene-2, isobutylene, the pentenes, heptenes, hexenes, octenes, nonenes, deceries, undecenes, dodecenes, tridecenes, tetradecenes, pentadecenes, hexadecenes, heptadecenes, octadecenes, nonadecenes, and eicosene. Propylene and the 4-carbon olefins are particularly preferred in the practice of this invention. Dimers and trimers—and low-molecular weight oligomers generally - of the lower alkenes such as ethylene, propylene, and the butenes also are suitable olefinic compounds in the practice of this branch of the invention.

The cycloalkenes and the substituted cycloalkenes comprise another class of olefinic compounds which may be used in the practice of our invention. Suitable alkenes include cyclopentene, cyclohexene, cyclooctene, cycloheptene, cyclononene, and cyclodecene. Among other illustrative cyclic olefinic compounds are cyclooctadiene, dicyclopentadiene, methylenecyclopropane, methylenecyclopentane, vinylcyclohexene, methylcyclopentene, ethylcyclopentene, propylcyclopentene, methylcyclohexene, methylcycloheptene, and so forth.

Aryl substituted alkenes also may be used generally and include materials such as styrene, 1-phenyl-1-propene, 1-phenyl-2-propene, 2-phenyl-1-propene, the phenyl butenes, phenyl pentenes, phenyl hexenes, phenyl heptenes, divinylbenzene, indene, stilbene, and so forth.

The olefinic compounds which may be used in the practice of our invention may bear other functional groups, either at the olefinic carbons or, more generally, at a position other than the olefinic carbon. For example, alcohols and ethers thereof may be among the functionalized olefinic compounds used as a feedstock in our invention, including such materials as allyl alcohol, allyl methyl ether, allyl ethyl ether, 2-buten-1-ol, 3-buten-2-ol, 3-buten-1-ol, cinnamyl alcohol, alkyl and aryl ethers of the buten-1-ols, 2-methyl-2-propene-1-ol, alkyl ethers of the latter such as the methyl, ethyl, propyl, and butyl ethers, as well as such ethers as the benzyl and phenyl ethers thereof, all of which serve to illustrate the presence of an hydroxyl or ether group in the olefinic compound. Allyl alcohol and their ethers are particularly important inasmuch as the product, glycidol and glycidyl ethers, are important chemical intermediates.

Haloalkenes also may be used in the practice of this invention, particularly where the halogen is not on an olefinic carbon. For example, allyl chloride and allyl bromide afford as the epoxidation product epichlorohydrin and epibromohydrin, resp., both of which are important articles of commerce.

Olefinic carboxylic acids and their esters are another class of compounds which may be used in the practice of our invention and may be exemplified by such materials as acrylic acid, alpha-methacrylic acid, 2-butenoic acid, 3-butenoic acid, 2-pentenoic acid, 3-pentenoic acid, 4-pentenoic acid, 2-methyl-2-butenoic acid, 3-methyl-2-butenoic acid, 2-methyl-3-butenoic acid, and so forth. Other unsaturated acids of particular mention as olefinic compounds subject to epoxidation by the process of our invention include cinnamic acid, maleic acid, and fumaric acid, and the large class of unsaturated fatty acids and their esters, especially triglycerides, represented by acids such as linoleic acid, linolenic acid, oleic acid, ricinoleic acid, erucic acid, palmitoleic acid, and the like.

Other functional groups may be present in the olefinic compound, especially at the non-olefinic carbons, including such functional groups as the sulfonic acid grouping and their corresponding esters, the nitrile grouping, nitro and ether grouping. Dienes also may be used in epoxidation, especially butadiene. Except in unusual circumstances it must be recognized that dienes can be expected to undergo epoxidation at either C=C bond, hence the selectivity of the epoxidation of dienes can be expected to be low with respect to formation of an epoxide at but one point in the molecule. Consequently dienes, and polyenes more generally, are not favored among the olefinic compounds for this reaction, principally because of the complexity of the resulting reaction mixture. On the other hand, where selectivity of double bond epoxidation is unimportant polyenes may be readily numbered as among the suitable substrates in our invention.

The epoxidizing agent of our invention may be any hydroperoxide, although hydrogen peroxide is preferred by far. Among the organic hydroperoxides may be mentioned the alkyl hydroperoxides, especially tertiary butyl hydroperoxide and, to a lesser extent, the hydroperoxide of ethylbenzene. Peracids form another class of organic compounds furnishing the peroxide linkage and among these peracetic acid, trifluoroperacetic acid, and perbenzoic acid are the most commonly employed peracids.

The primary oxidizing agent which is used in the practice of this invention is hydrogen peroxide, especially as aqueous solutions. Thirty weight percent solutions of hydrogen peroxide in water have been standard in the prior art, but their disadvantage is that of cost. One important advantage of the process of our invention is that our catalysts are effective in bringing about epoxidation even with dilute aqueous hydrogen peroxide as the oxidizing agent. Thus, even 2 weight percent aqueous hydrogen peroxide solutions may be employed to convert olefinic compounds to their epoxide in yields in excess of 90% and with virtually 100% efficiency in utilization of hydrogen peroxide. In general, aqueous solutions containing as little as about 2% and as much as about 70 weight percent hydrogen peroxide may be used, although hydrogen peroxide concentrations of 2–15 weight percent are far more common, and concentrations of 2–10 weight percent are preferred. Where the olefinic compound is epoxidized under heterogeneous conditions, it behooves one to use as concentrated a hydrogen peroxide as is readily available, which generally translates to the use of a 30% hydrogen peroxide solution. Nonetheless, we need to emphasize again that the concentration of the hydrogen peroxide used as the epoxidizing agent is not a controlling factor in the practice of our invention, that dilute hydrogen peroxide solutions can be readily employed, and that the concentration of hydrogen peroxide used is dictated by secondary factors extraneous to our invention itself.

The catalyst which we have found to be particularly effective in epoxidation is a mixture of a titanosilicate and titania whose particle size is an essential feature of catalyst activity. More particularly, we believe the catalyst is a mixture of titania and a titanosilicalite—i.e., silicalite containing titanium in its framework—where each has an average particle size ("diameter") no more than about 0.5 microns. It is preferable that each of the particles have an average size no more than about 0.3 microns and even more preferable that at least 80 percent of the particles be no more than about 0.3 microns. In practice we have found that titanosilicalite particles may be readily made with a remarkably uniform diameter of about 0.2 microns, and when in admixture with titania particles whose diameter is in the 0.1–0.3 micron range the resulting catalyst shows appreciably greater activity than either the titanosilicalite alone or a titanosilicalite-titania mixture whose titanosilicalite particles are appreciably outside the range stated above. In a preferred embodiment at least 80% of both the titanosilicalite and the titania particles are in the 0.1 to 0.3 micron range.

We believe the key to the outstanding properties of our catalyst is the titanosilicalite particle size, and we have found few methods which afford titanosilicalite particles of the requisite size. The catalyst of our invention may be made as follows. In a preferred mode it is desired to deposit small titanium-containing particles on titania prior to the crystallization of a titanosilicate in its presence. However, it needs to be emphasized that this is not a prerequisite to the success of our invention, but merely a variant which we prefer. In this variant high purity titania is first impregnated with a titanium source, such as titanocene or a titanium alkoxide, and then dried. The impregnated titania is then mixed with a gel containing both a titanium and a silicon source, such as titanium t-butoxide and tetraethyl silicate, respectively. This powder-in-gel mixture is then crystallized under hydrothermal conditions, which means stirring the powder-in-gel mixture at temperatures of between about 150° and about 200° C. and pressures between about 100 and about 200 psig for a time usually from about 2 to about 10 days. Following crystallization the solid is collected, washed well, generally with water, dried, and then calcined. Although we generally use a temperature in the interval of 500° to about 550° C., it is not believed that the calcination temperature is a critical variable in the successful preparation of our catalyst and we believe temperatures in the range of 400°–700° C. will suffice.

The gel of titanium and silicon sources contains these two elements at a Si:Ti atom ratio of from about 5 up to about 100, with ratios of 10–40 being the most usual ones. The total amount of titanosilicalite crystallized and titania particles affords a final composite whose composition as titania/silica can be expressed as

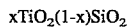

$$xTiO_2(1-x)SiO_2$$

where x may be as low as about 0.1, but usually at least 0.5, and as high as about 0.98, with the range between about 0.7 and about 0.8 favored in the practice of this invention.

Catalysts prepared as described above may be used directly or may be ion exchanged with a cation such as an alkali metal or alkaline earth cation. Cation exchange appears to somewhat increase selectivity but this variant is considered optional rather than essential and mandatory. Where cation exchanged material is used exchange with an alkali metal cation, especially that of sodium and potassium, is preferred. Exchange with an alkaline earth metal cation is another variant, one in which the use of magnesium and calcium is preferred.

Olefinic compounds are oxidized using principally hydrogen peroxide as the oxidizing agent in the presence of the aforedescribed catalyst under epoxidation reaction conditions. Such reaction conditions include a temperature as low as about 0° C. up to as high as about 100° C. Epoxidation may be conducted at atmospheric pressure. A major reason to perform the epoxidation at elevated pressure is to increase the solubility of gaseous reactants in the reaction medium. For example, where propylene is epoxidized without the use of a cosolvent increased pressure leads to an increased solubility of the propylene in aqueous solution with an increase in overall rate of propylene epoxide formation.

Epoxidation may be performed according to our invention in either a batch or continuous mode. For example, in a batch mode the olefinic compound, either alone or in an organic solvent, is mixed with an aqueous hydrogen peroxide solution in the presence of an effective amount of a titania supported titanosilicate. The amount of titania supported titanosilicate used per mole of carbon-carbon double bond to be epoxidized may be as low as about 3 grams per mole. There is no theoretical limit to the maximum amount of titanosilicate to be used, although as a practical matter there is no benefit from using more than about 30 grams per mole of carbon-carbon double bond. The reaction mixture is stirred well at temperatures between 0° C. up to as high as about 100° C. The hydrogen peroxide may be present at a concentration as low as about 2 weight percent and as high as about 50 weight percent. Whether the hydrogen peroxide or the olefinic compound is present in excess depends upon the nature of the olefinic compound as well as its cost. For example, where propylene is being epoxidized, unreacted gaseous propylene may be readily recovered and recycled. In such an instance it is advantageous to have the olefinic compound in molar excess, perhaps as much as 2–10 moles per mole of hydrogen peroxide. However, where a rather expensive, or relatively unavailable olefinic compound is being epoxidized, it may be highly advantageous to use hydrogen peroxide in molar excess, perhaps in amounts as little as 5–10% molar excess, although molar ratios of up to 10 may be employed. In general, then, the molar ratio of olefinic compound to hydrogen peroxide may range from 1:10 to 10: 1.

Where the reaction is performed in a continuous mode one may employ any of the conventional process techniques currently known. These include use of a fixed bed process, a continuous stirrer tank reactor process, a radial bed reactor process, and so on. In such cases the catalyst of our invention may be used as pellets, extrudates, spheres, and the like. When our titania supported titanosilicate is used in such forms it is preferable to incorporate a binder for preserving and enhancing catalyst integrity. Conventional binders include silica, alumina, silica-alumina, and various clays, but since such conventional materials are well known to those skilled in the binder art no further detailed discussion will be given.

The following examples merely illustrate the process of our invention and are not intended to limit it in any way. Variants of the following examples may be readily envisioned, and are to be considered as within the scope of our invention.

EXAMPLE 1

Preparation of the titania-titanosilicalite mixture. The following description is representative of the procedure used to prepare the catalysts of this invention. High purity titania may be first impregnated with a titanium source, such as titanocene or titanium butoxide by mixing 500 g of titania with 2 g of the titanium source in 200 cc of a solvent, such as isopropyl alcohol. Solvent was evaporated and the resulting solid was dried in a vacuum oven overnight at 120° C.

A gel from silicon and titanium sources was prepared as follows. Tetraethyl orthosilicate (682.5 g in 300 cc water) and 300 cc isopropyl alcohol was cooled to 10°–15° C., and to this was added 150 g of 40 weight percent tetrapropyl ammonium hydroxide and 150 g water to partly hydrolyze the silicon source. To this mixture was added dropwise with vigorous stirring a solution of 33.6 g titanium butoxide in 150 mL isopropyl alcohol. The clear yellow liquid was stirred for about 1 hour at room temperature, after which 450 g of 40 weight percent tetrapropyl ammonium hydroxide and 1650 g distilled water were added to complete the hydrolysis at 80° C. for about 6 hours.

Approximately 500 g of impregnated titania and 2,000 cc of the gel were added to an autoclave with stirring and crystallization was permitted to proceed under hydrothermal conditions (175° C. for 3 days at 250–300 psi pressure). The crystalline solid obtained was centrifuged, washed with distilled water, dried, and calcined at 550° C. in air for 5 hours.

Using the foregoing procedure a number of titania-titanosilicalite mixtures were prepared having a range of silicon content representing different values of x in the formula $$xTiO_2(1-x)SiO_2$$

The percentages of titanium, silicon, and the corresponding value of x in the various preparations is summarized in Table 1.

TABLE 1

Analytical Data for Titania-titanosilicalites

| Sample | Si, wt % | Ti, wt % | $x^{a,b}$ |
|---|---|---|---|
| 1 | 8.79 | 49.7 | 0.77 |
| 2 | 6.73 | 45.9 | 0.80 |
| 3 | 1.22 | 57.4 | 0.97 |
| 4 | 36.7 | 9.76 | 0.13 |
| 5 | 17.6 | 37.1 | 0.55 |
| 6 | 9.98 | 44.9 | 0.72 |

[a]Refers to formula $xTiO_2(1-x)SiO_2$
[b]Calculated from the weight ratio Ti/Si. The atom ratio, R, of Ti:Si is related to x by the formula, $R = x/(1-x)$ Framework titanium has been characterized by a charge transfer peak in the ultraviolet at 220 nm whereas extra framework titanium gives a peak usually at 275 nm or greater. Consequently, ultraviolet diffuse reflectance spectroscopy has been used to characterize the amount of framework titanium in various molecular sieves. See C. B. Khouw, H. X. Li, and M. E. Davis: Symposium on Catalytic Selective Oxidation, pp. 136 et. ff. (1992); D. R. Chuybrechts and P. A. Jakobs: J. Molecular Cat., 71, 129–147 (1992). The ultraviolet reflectants spectra of a sample was obtained and a difference spectrum from $TiO_2$ (anatase) was generated. The difference spectrum clearly showed absorbance at 220 nm, which also was observed in a sample of a titanosilicalite prepared in the absence of titania.

Infrared spectroscopy also has been utilized in analyzing for framework titanium since a peak at 960 cm$^{-1}$ is considered a fingerprint for framework titanium. Examination of a pellet of our catalyst in a potassium bromide wafer showed a band at 960 cm$^{-1}$, again indicating the presence of framework titanium.

Examination of the catalyst by scanning electron microscopy showed titanosilicalite particles of about 0.2 microns (with agglomerates of approximately 100 microns) with a remarkably small size distribution. The size of the titania particles were in the 0.1–0.3 micron range.

Examination of the catalyst by scanning transmission electron microscopy was even more informative. All of the silicon-rich particles examined showed the presence of titanium. However, when the titania particles were analyzed no silicon was detected. Thus, titanium appears definitely to be associated with the silicalite. The amount of Ti was 1.51 ±0.21 atom percent where the amount of Si+Ti=100%. The variability in titanium as determined by the standard deviation is somewhat greater than one would expect for a homogeneous sample, which suggests some variability of titanium concentration between silicon-rich particles. No titanium surface enrichment of the silicon-rich particles was observed. Thus, the titanium probably is uniformly concentrated throughout the particles, but not necessarily between particles. When examining a cross section of a large agglomerate one finds either titania or silicalite particles. Thus, one can conclude that there are discrete titanosilicalite and titania particles of approximately the same size and randomly distributed throughout the sample.

EXAMPLE 2

Oxidation of propylene; general procedure. To a Parr reactor was added 40 g of 30 weight percent aqueous hydrogen peroxide, 200 g methanol as a cosolvent, and 2.5–10 g of catalyst. When the desired temperature was reached, liquid propylene was added to the reactor along with nitrogen to a total pressure of 500 psi. Because the epoxidation is exothermic, the reaction mixture was internally cooled where necessary. Samples were taken periodically and analyzed by gas chromatography. The reaction generally was conducted in the interval of 40°–60° C. with a molar ratio of propylene:hydrogen peroxide of 5:1. Hydrogen peroxide concentration was measured iodometrically; propylene oxide yield (based on hydrogen peroxide) was determined by gas chromatography.

EXAMPLE 3

Comparison of titania supported titanosilicates and TS-1. In this example there is compared directly TS-1, a 15:85 mixture of TS-1 and titania, and three titanosilicates, Catalysts A, B, and C supported on titania differing in their method of preparation. Catalyst C was prepared as described in Example 1 with titania impregnation by a Ti source prior to deposition of the titanosilicate, and corresponds to sample 2 of Table 1. Catalyst B was prepared without such impregnation and has virtually identical silicon and titanium analysis (x=0.80). Where titania was used a uniform 0.2 micron sized particle was utilized. The results, summarized in Table 2, show quite clearly that not only do the catalysts of our invention show a far greater activity than do the TS-1 catalysts of the prior art, but also are far superior to a physical mixture of TS-1 and titania. It also is interesting to note that the yield with the catalysts of our invention are much greater than afforded by the other materials. Reactions were performed at 40° C. using 1.25 g of catalyst, 40 g of 30 weight percent $H_2O_2$, 200 g methanol and 73 g propylene.

TABLE 2

Comparison of TS-1 with Titania Supported Titanosilicates

| | Catalyst; % Propylene Oxide Formed | | | |
|---|---|---|---|---|
| Time (hrs) | TS-1[a] | A[b] | B[c] | C[c] |
| 0 | 0 | 0 | 0 | 0 |
| 0.25 | 5.9 | 9.2 | 38.6 | 40.9 |
| 0.5 | 16.1 | 18.9 | 51.4 | 66.2 |
| 1 | 21.1 | 23.9 | 67.1 | 71.7 |
| 3 | 28.5 | 33.1 | 70.8 | 80.9 |
| 0 | 34.9 | 38.6 | 82.9 | 90.1 |

[a]Titanium silicalite according to prior art (TS-1).
[b]Physical mixture of 0.188 g TS-1 and 1.07 g $TiO_2$.?
[c]See text.

EXAMPLE 4

Effect of reaction temperature, contact time, and catalyst amount on propylene oxide yield. In this example contact time, reaction temperature, and the amount of catalyst used was varied in order to study their effects on propylene oxide yield. Tables 3 and 4 summarize these results. The catalyst used was sample 6 of Table 1 and had a surface area of 91 $m^2/g$.

TABLE 3

Effect of Temperature on Propylene Oxide Formation
(10 g. catalyst)

| | % Propylene Oxide Formed | | |
|---|---|---|---|
| Time (hours) | 30° C. | 40° C. | 50° C. |
| 1 | 46 | 62 | 79 |
| 3 | 62 | 74 | 81 |
| 4 | 73 | 79 | 85 |
| 5 | 80 | 85 | 92 |
| 6 | 93 | 93 | 95 |
| $H_2O_2$ Conversion after 6 hours | 100 | 100 | 100 |

TABLE 4

Effect of Catalyst Amount on Propylene Oxide Formation at 40° C.

| | Catalyst Amount C | | |
|---|---|---|---|
| Time (hours) | 2.5 g | 5 g | 10 g |
| 1 | 35 | 42 | 61 |
| 3 | 41.3 | 58.5 | 74 |
| 4 | 45.7 | 60 | 79 |
| 5 | 50.8 | 67.5 | 81 |
| 6 | 60.9 | 87 | 93 |
| $H_2O_2$ Conversion after 6 hours | 63 | 90 | 100 |

EXAMPLE 5

Catalyst reusability. The general conditions for epoxidation were those described in Example 2. After each epoxidation reaction, the catalyst (sample 2 of Table 1) was recovered by centrifugation and reused, without any additional treatment, in a subsequent epoxidation. Table 5 shows the yield of propylene oxide after 6 hours reaction attained after 1, 2, 3 and 4 reuses. The data show quite clearly that the catalyst manifests virtually no decrease in activity.

TABLE 5

Catalyst Reusability

| | | Propylene Oxide | | |
|---|---|---|---|---|
| Cycle | T, °C. | % Yield | % Selectivity | % $H_2O_2$ Conversion |
| 1 | 60 | 90 | 91 | 100 |
| 2 | 40–60 | 93 | 93 | 100 |
| 3 | 40–60 | 98 | 94 | 100 |
| 4 | 40 | 94 | 94 | 97 |

What is claimed is:

1. A process for the epoxidation of a carbon-carbon double bond in an olefinic compound comprising reacting under epoxide-forming conditions the olefinic compound with a hydroperoxide in the presence of a catalyst comprising a mixture of first particles of a titanium silicalite and second particles of titania, said first and second particles having an average particle size no more than about 0.5 microns in diameter.

2. The process of claim 1 where epoxide-forming conditions include a temperature between about 0° C. and about 100° C.

3. The process of claim 1 where the hydroperoxide is hydrogen peroxide.

4. The process of claim 3 where the hydrogen peroxide is at a concentration from about 2 weight percent up to about 50 weight percent.

5. The process of claim 3 where the hydrogen peroxide is at a concentration between about 2 and about 15 weight percent.

6. The process of claim 5 where the hydrogen peroxide is at a concentration between about 2 and about 10 weight percent.

7. The process of claim 1 where the olefinic compound is an alkene or cycloalkene.

8. The process of claim 7 where the alkene is propylene.

9. The process of claim 7 where the cycloalkene is cyclohexene.

10. The process of claim 1 where the olefinic compound is an alcohol.

11. The process of claim 10 where the alcohol is allyl alcohol.

12. The process of claim 1 where the olefinic compound is a carboxylic acid, a carboxylic acid anhydride, or an ester of a carboxylic acid.

13. The process of claim 12 where the carboxylic acid or an ester thereof is maleic acid, fumaric acid, esters thereof, or any mixture thereof.

14. The process of claim 1 further characterized in that the olefinic compound is reacted as a solution in an organic solvent.

15. The process of claim 1 where the total ratio of titanium to silicon atoms in the catalyst is from about 1 to about 49.

16. The process of claim 1 where the first and second particles have an average particle size no more than about 0.3 microns.

17. The process of claim 1 where at least 80% of the particles are no more than 0.3 microns in size.

* * * * *